United States Patent [19]

Snyder

[11] 4,212,295
[45] Jul. 15, 1980

[54] MOISTURE RESPONSIVE PAD FOR TREATMENT OF ENURESIS

[75] Inventor: Joe W. Snyder, Newberg, Oreg.

[73] Assignee: Nite Train-R Enterprises, Inc., Newberg, Oreg.

[21] Appl. No.: 905,192

[22] Filed: May 12, 1978

[51] Int. Cl.² ...................... A61B 19/00; H01H 29/00
[52] U.S. Cl. ............................... 128/138 A; 340/573; 340/604; 200/61.05
[58] Field of Search ............ 128/138 A, 138 R, 2.1 Z, 128/2.1 R, 417, 419 R, 734, 639, 640, 805; 340/573, 604; 200/61.05

[56] References Cited

U.S. PATENT DOCUMENTS

| | | | |
|---|---|---|---|
| 2,046,080 | 6/1936 | McClellan | 128/138 A |
| 2,127,538 | 8/1938 | Seiger | 128/138 A |
| 2,321,683 | 6/1943 | Jacobson | 128/138 A |
| 2,668,202 | 2/1954 | Kaplan | 128/138 A |
| 2,687,721 | 8/1954 | Ellison | 128/138 A |
| 2,874,695 | 2/1959 | Vaniman | 128/138 A |
| 2,907,841 | 10/1959 | Campbell | 128/138 A |
| 3,441,019 | 4/1969 | Snyder | 128/138 A |
| 3,678,928 | 7/1972 | Mozes | 128/138 A |
| 3,741,219 | 6/1973 | Sessions | 128/417 |
| 3,891,786 | 10/1973 | Conklin | 428/136 |

FOREIGN PATENT DOCUMENTS

| | | | |
|---|---|---|---|
| 549869 | 8/1956 | Belgium | 340/604 |
| 521803 | 6/1952 | Canada | 340/604 |
| 77306 | 4/1918 | Switzerland | 340/604 |
| 680088 | 10/1952 | United Kingdom | 128/138 A |
| 145704 | 12/1960 | U.S.S.R. | 340/604 |

*Primary Examiner*—Robert W. Michell
*Assistant Examiner*—Arthur S. Rose
*Attorney, Agent, or Firm*—Wells, St. John & Roberts

[57] ABSTRACT

A pad adapted for use with an electrically actuated signal where the pad acts as a sensor to detect involuntary emission of urine. It is designed to be worn adjacent to the body of the user. It includes a central layer of closed cell foam sandwiched between two outer layers, each fabricated from a sheet having an electrically conductive surface. At least one of the outer layers and the foam layer have discrete apertures formed through them in registry with one another to receive and collect discharged urine. The urine bridges the gap between the conductive surfaces and thereby completes a signal circuit.

3 Claims, 4 Drawing Figures

MOISTURE RESPONSIVE PAD FOR TREATMENT OF ENURESIS

BACKGROUND OF THE INVENTION

Enuresis or involuntary release of urine, and particularly nighttime enuresis, is a common problem among young children and adolescents. It is a very typical problem among boys. It is also encountered in caring for the elderly. Much literature has been devoted to the causes of such problems, which are complex and often related to both psychological and related physical problems. The resulting symptoms and "bedwetting" are troublesome both to the person involved and to those caring for him.

Many different devices have been proposed to assist in correcting this problem. One solution has been to use pads placed on a bed which sound an alarm when wet. Obviously such pads cannot be used other than on beds or similar support surfaces, and are not effective in assisting ambulatory elderly patients. More importantly, such devices have a long reaction time between the release of urine and the time when the bed or pad becomes sufficiently wetted to activate a signal. This time lag is so great that the subsequent awakening of the child or alerting of the person is too late to effectively remedy the situation. To be effective, such an alarm must sound as quickly as possible after the initial release or discharge of urine. The alarm must be effective in waking the child very promptly, since the tendency to sleep soundly often accompanies symptoms of enuresis.

In U.S. Pat. Nos. 3,441,019 and 3,508,234 I have disclosed alarm devices triggered by the bridging of spaced electrically conductive surfaces on devices worn by the person. No soaking or penetration of material substances is necessary. Such devices have been effective in awakening children and users immediately upon hearing the signal. They have therefore been able to hasten to the bathroom, sparing the usual soaking of night clothing and bedding. The reflex action generated by use of this device has been most effective when used by a child capable of manipulating and cleaning the apparatus when so awakened. Similar alarms have been successful in aiding in the care of aged persons who have lost control of urinary functions. An audible alarm can alert nurses and attendants and assist in the sanitary care of such persons.

The present apparatus provides a sanitary device which can be reused and easily maintained in a clean condition. It is flexible and soft, eliminating the use of a rigid casing adjacent to the body. After use, the disclosed pad can be easily "reset" by simply drying its surfaces by application of a dry tissue. No elements need be assembled or disassembled. The pad provides a soft, comfortable, flexible device which will hug the body contours of either sex, regardless of body position or attitude; whether sitting, standing, or lying in bed. It will always be in proper position to intercept the first issue of urine. The pad is lightweight, is compact and acceptable to people of all ages. It requires no special garments.

DESCRIPTION OF A PREFERRED EMBODIMENT

Figure 1:
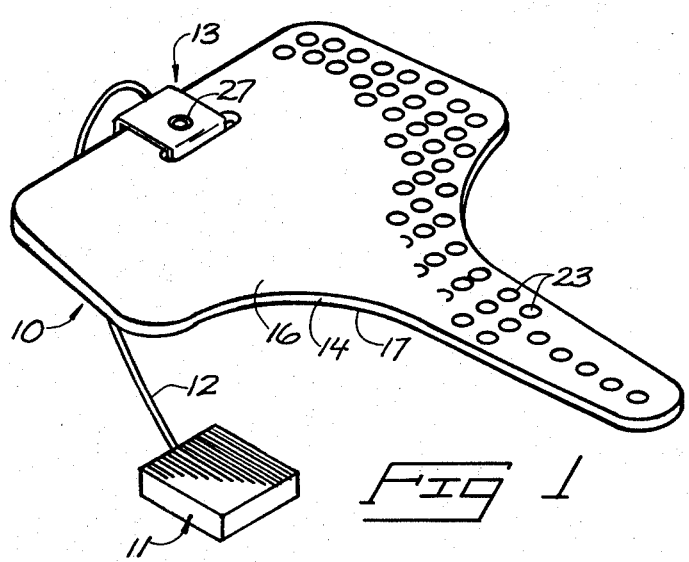
FIG. 1 is a perspective view showing the pad in combination with a signaling device.

The pad which is the subject of this disclosure is generally indicated in the drawings by the reference numeral 10. As can be seen in FIG. 1, the periphery of pad 10 is designed to enable it to be fitted within an undergarment worn by a user. The apertured pad surface is preferably located in direct contact with the user's body within the crotch portion of snugly fitting panties or underpants. Pad 10 can be used by male or female users, and will be held in place adjacent to the urethra without any accessory attachments, straps, pins or clips.

Pad 10 is used in conjunction with an electrically actuated signaling device shown generally at 11. The container shown at 11 would include batteries and a solid state miniature buzzer or other suitable audible alarm circuit. The circuit preferably sounds an intermittent signal which has been found to be more effective in awakening a sleeping user. Wires 12 connect the signaling device 11 to pad 10 through a releasable clip 13.

The details of the signaling circuit or device 11 are not set out herein, but are generally similar to those described in U.S. Pat. Nos. 3,441,019 and 3,508,234 which are hereby incorporated by reference. When desired, an external jack on the signaling device 11 can be used in conjunction with a miniature earphone (not shown) to direct the signal in close proximity to the ear of the user, which makes it even more effective.

Figure 2:
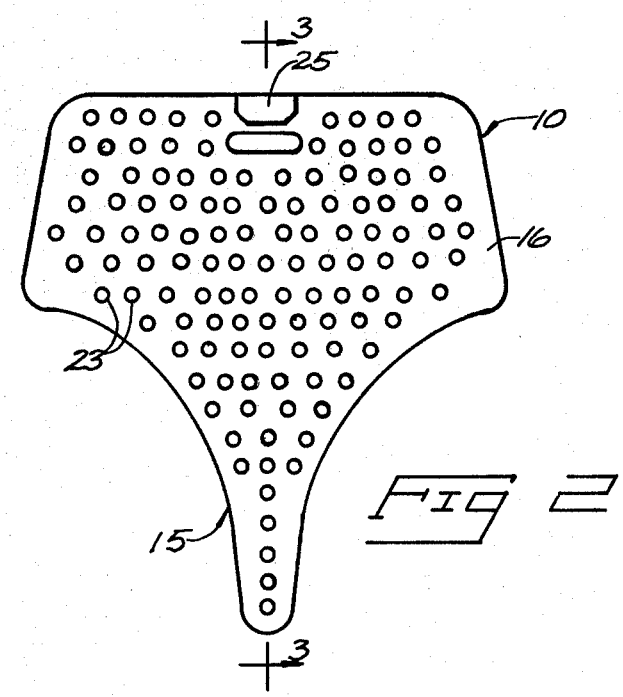
FIG. 2 is a plan view of the pad.

The pad 10 is built about a central insulating layer 14. Layer 14 is molded, cut, or otherwise fabricated as a sheet of closed cell elastomeric foam. Layer 14 is both flexible and compressible. It should be made of nonabsorbent closed cell foam to prevent liquid from being absorbed therein and to present roughened surfaces which assist in spreading droplets of urine across the thickness of the layer 14. The material of layer 14 is electrically nonconductive and thereby presents a central insulating layer in pad 10. It has a constant thickness between oppositely facing parallel surfaces. Its peripheral configuration, as can be seen in FIG. 2, enables it to be fitted within an undergarment worn by a user. In this regard, its shape might be described as a "pear-shaped peripheral configuration", which includes a wide upper section and a protruding narrow section centered thereon. As is evident from the drawings, the narrow section shown at 15 is adapted to be fitted between the legs of the user.

The central insulating layer 14 is sandwiched between a first electrode layer 16 and a second electrode layer 17. Each comprises a continuous sheet of flexible material which is both nonabsorbent and liquid impervious. Each electrode layer 16, 17 has an electrically conductive surface facing outward to one side thereof and an electrically nonconductive surface facing outward to its remaining side. A conductive surface of sheet 16 is shown at 18. Its nonconductive or insulating surface is shown at 20. The conductive surface of layer 17 is shown at 21. Its nonconductive or insulating surface is shown at 22.

A very suitable material for the electrode layers 16, 17 is an electrically conductive fabric disclosed in U.S. Pat. No. 3,891,786 which was issued June 24, 1976. This fabric comprises nylon filaments sandwiched between wear resistant vinyl surfacings, one surface material being an electrical insulator and the other being an electrical conductor.

The surfaces 18, 21 of the electrode layers 16, 17 are bonded to the respective outer surfaces of the central insulating layer 14. Any suitable bonding technique of a permanent nature can be utilized, such as chemical bonding by a flexible adhesive material.

The layer 16 and the center insulating layer 14 have a plurality of discrete open apertures 23 formed through the respective thicknesses thereof, each aperture being in registration through both layers. As shown, identical apertures are formed in both layers 14 and 16 in identical spacial positions. The layer 17 is uninterrupted and continuous across the back face of the pad 10, sealing off the apertures of the center layer 14 along the outer surface thereof. Thus, a series of pockets are formed through layers 16 and 14 facing toward one side of pad 10 for reception of urine. It is layer 16 which is placed in direct contact with the user's body when in place within an undergarment.

Figure 3:
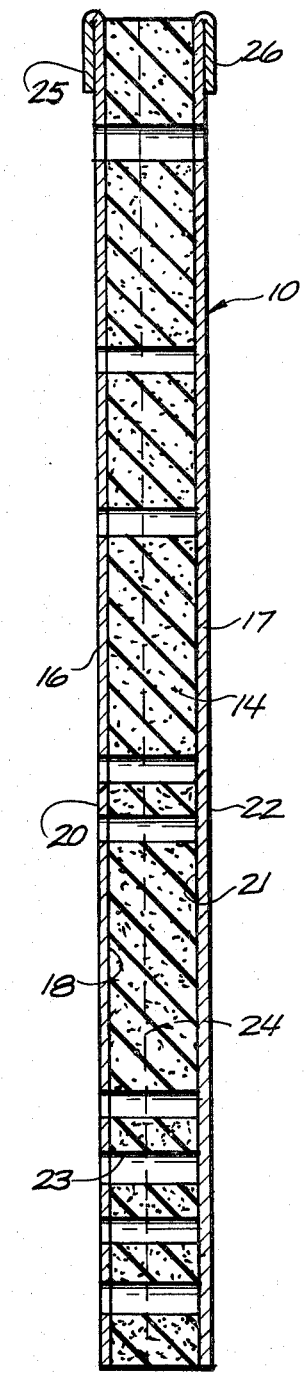
FIG. 3 is an enlarged sectional view taken along line 3—3 in FIG. 2.
Figure 4:
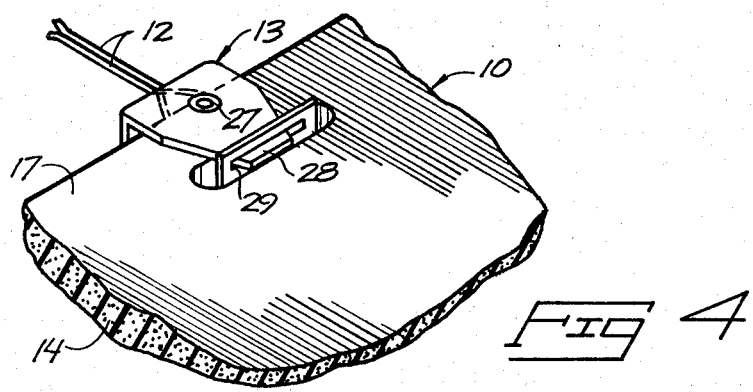
FIG. 4 is a fragmentary perspective view of the attachment electrical clip.

The apertures 23 are circular in cross section and the open pockets formed through layers 16, 14 are therefore of a cylindrical shape. It has been found advisable that the radius of each aperture 23 be less than 60% of the thickness of the layer 14. A suitable thickness for layer 14 has been found to be $\frac{3}{8}''$. Using thicknesses substantially less than this risks the possibility that flaccid tissue or skin of the user might intrude far enough through one or more apertures to make electrical contact with the conductive surface 21 of the layer 17 and thereby cause the signaling device 11 to sound unnecessarily. The size relationship spelled out above assures that the opening across each aperture 23 will not exceed its depth when the user is lying face downward, which results in partial compressing of the soft, closed cell central layer 14. The phantom line 24 shown in FIG. 3 illustrates the 60% depth of the pad 10 from the compressed location of surface 18 to surface 21.

In order to assure that release of urine is signaled as quickly as possible, the apertures 23 are arranged about the area of layer 16 in a substantially continuous pattern.

The peripheral configurations of the three layers 14, 17 and 18 correspond in both size and shape, resulting in a sandwich pad configuration wherein the conductive surfaces 18, 21 are spaced apart by a constant distance equal to the thickness of the central insulating layer 14.

To permit replacement of pad 10 as easily as possible, a releasable clip 13 can be used in conjunction with it. Pad 10 facilitates electrical attachment to clip 13 by the provision of extensions of tabs 25, 26 which are formed integrally at the upper edge of the layers 16, 17. Each tab 25, 26 is folded over upon the respective outer surface of the sheet on which they are formed, thereby exposing an area of its electrically conductive surface for connection purposes.

Clip 13 is preferably fabricated or molded of an electrically insulated insulating material, such as plastic resin. Electrical contacts 27 are imbedded at each side of clip 13 for engagement by wires 12. An integral hook 28 formed at one side of clip 13 releasably interlocks with its opposite side through a complementary aperture shown at 29. The resiliency and relative thickness between the opposed sides of clip 13 assure compressive engagement between contacts 27 and the exposed conductive surfaces at the tabs 25, 26. Clip 13 can be readily disengaged to permit substitution of pads 10 when necessary.

In use, the pad 10 is worn adjacent to the body of the user. Upon release of urine, the first droplet that bridges the conductive surface 18, 21 will result in sounding of the alarm through operation of the signaling device 11. This will either alert or awaken the user or an attendant, and prompt attention will permit the user to subsequently urinate without wetting the clothes he is wearing. The pad 10 has the capability of holding as much as $\frac{1}{8}$ cup of urine within the volume of apertures 23 if the foam layer is $\frac{3}{8}''$ thick. The continuous cover provided by the layer 17 prevents escape of the urine to the surrounding garments.

Since the materials of the pad 10 do not absorb any moisture, it can be easily restored to its dry condition by means of absorbent tissue or toweling. The surfaces of layer 16 and the aperture surfaces can be readily dried by pressing the drying medium into the apertures 23. Their depth will be reduced by slight finger pressure so that all interior surfaces are readily contacted and dried. The pad 10 can then be replaced in the undergarments and reused immediately.

Various change might be made in the device without modifying the basic concept embodied in its structure. For this reason, only the following claims are intended to define the scope of the invention disclosed herein.

Having described my invention, I claim:

1. A moisture responsive pad for signaling involuntary emission of droplets of urine when worn by a user and used in combination with an electrically activated signaling apparatus, comprising:
    a central insulating layer formed as a sheet of flexible, nonabsorbent closed cell elastomeric foam material having a constant thickness between oppositely facing parallel surfaces, the central layer being compressible and electrically nonconductive;
    first and second electrode layers each comprising a continuous sheet of flexible nonabsorbent liquid impervious material having an electrically conductive surface;
    said first electrode layer being bonded to a first surface of said central layer;
    said first electrode layer and said central insulating layer having a plurality of discrete open apertures formed therethrough in corresponding registration with one another;
    said apertures having diameters less than the thickness of the central insulating layer;
    said second electrode layer being bonded to the remaining surface of said central insulating layer such that the conductive surface contacts the central insulating layer;
    the peripheral configurations of the first and second electrode layers corresponding in both size and shape to the peripheral configuration of the central insulating layer, whereby the respective electrically conductive surfaces of said first and second electrode layers are spaced apart;
    said pad having a contoured peripheral configuration including a wide upper section and a protruding narrow lower section centered thereon, enabling the pad to be fitted within the crotch of an undergarment by a user;
    said second electrode layer being a continuous noninterrupted sheet of material sealing off the apertures of said center insulating layer along said remaining surface thereof; and wherein the walls of the open apertures of the central closed cell elastomeric foam insulating layer have uniformly roughened surfaces extending between the electrode layers which assist in spreading the droplets of urine across the thickness of the insulating layer to provide an electrically conductive path between the first and second electrode layers.

2. A pad as set out in claim 1 wherein the electrically conductive surfaces of said first and second electrode layers are bonded to the respective surfaces of the central insulating layer and are thereby spaced apart by a distance equal to the thickness of the central insulating layer.

3. A pad as set out in claim 2 wherein said first and second electrode layers each have corresponding integral tabs folded over upon the respective second surfaces thereof, whereby an area of the electrically conductive surface of each layer is exposed for electrical connection purposes.

* * * * *